United States Patent [19]

Tate et al.

[11] Patent Number: 5,679,813
[45] Date of Patent: Oct. 21, 1997

[54] METAL ORGANIC COMPOUNDS AND THEIR USE

[75] Inventors: Philip Edward Russell Tate, Hazel Grove; John William Prince, Whitworth; John Michael Hilton, Bolton, all of United Kingdom

[73] Assignee: Rhone-Poulenc Chemicals Limited, Hertfordshire, United Kingdom

[21] Appl. No.: 747,814

[22] Filed: Nov. 13, 1996

Related U.S. Application Data

[62] Division of Ser. No. 491,199, Jun. 16, 1995, Pat. No. 5,607,991.

[30] Foreign Application Priority Data

Jun. 20, 1994 [GB] United Kingdom ............... 9412363

[51] Int. Cl.$^6$ ................ C07F 5/02; C07F 15/04; C07F 15/06
[52] U.S. Cl. ........................................ 556/7; 556/28
[58] Field of Search ............................ 556/28, 7

[56] References Cited

U.S. PATENT DOCUMENTS

| | | | |
|---|---|---|---|
| 4,376,838 | 3/1983 | Davis et al. | 524/184 |
| 4,588,766 | 5/1986 | Tate | 524/176 |
| 4,609,499 | 9/1986 | Esashi et al. | 260/414 |
| 4,684,421 | 8/1987 | Tate | 156/124 |
| 5,276,172 | 1/1994 | Tate et al. | 556/28 |
| 5,607,991 | 3/1997 | Tate et al. | 524/184 |

OTHER PUBLICATIONS

Tate, "Cobalt Promoters Hold Firm," European Rubber Journal, pp. 28 and 31, Apr. 1986.
Tate, "Cobalt Adhesion Promoters, Past, Present and Future," Paper Presented to the Rubber Division, American Chemical Society 129th Meeting, New York, Apr. 1986.

*Primary Examiner*—Porfirio Nazario-Gonzalez
*Attorney, Agent, or Firm*—Finnegan, Henderson, Farabow, Garrett & Dunner, L.L.P.

[57] ABSTRACT

Metal organic compounds containing both cobalt and nickel bound to boron are effective adhesion promoters for bonding rubber to brass-coated metal used as a reinforcement.

5 Claims, No Drawings

METAL ORGANIC COMPOUNDS AND THEIR USE

This is a division of application Ser. No. 08/491,199, filed Jun. 16, 1995 now U.S. Pat. No. 5,607,996.

This invention relates to metal organic compounds, compositions containing them, and their use.

Compounds containing three atoms of a divalent metal such as cobalt, each linked through oxygen atoms to a boron atom and comprising monocarboxylic acid residues bonded to the metal are known additives for incorporation into rubber skim stock to improve adhesion of the rubber to brass-coated reinforcing wires.

European specification No. 0,148,782 describes metal organic compounds of this kind made by heating at 100° C. to 250° C. a nickel or cobalt salt of a carboxylic acid of from 3 to 24 carbon atoms with an alkaline earth metal borate.

European specification No. 0,150,840 describes cobalt boron compounds of the formula:

$$B(OCOY)_3$$

where Y is the residue of a resin acid, a naphthenic acid or an aliphatic carboxylic acid of 7 to 24 carbon atoms.

European specification No. 0,466,448 describes metal organic compounds of formula:

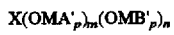

$$X(OMA'_p)_m(OMB'_p)_n$$

where X is boron or phosphorus, M is cobalt, nickel or bismuth, B' is a residue of aromatic carboxylic acid of 7 to 11 carbon atoms, A' is a residue of an aliphatic carboxylic of 7 to 11 carbon atoms, p is 1 or 2, n is 0.5 to 2, and m is (3-n).

In these known compounds the preferred metal is cobalt which is known to provide the best performance in the stated utility of improving adhesion of rubber to brass-coated steel, used as a reinforcement.

Nickel is known to give products which have inferior properties to those containing cobalt. Nevertheless, because nickel is ordinarily cheaper than cobalt, the possibility of replacing part of the cobalt by nickel has been investigated.

One of the present inventors, in a paper presented to the Rubber Division of the American Chemical Society in New York, U.S.A. in April 1986, presented data showing that if a nickel boron acylate is mixed with a cobalt boron acylate in a cobalt: nickel ratio of 2:1, while the performance of the mixture expressed as a percentage of the performance of the pure cobalt compound was reduced to 96%, the cost of the mixture at the then prevailing prices of cobalt and nickel, was reduced to 91%. Thus, it appeared that replacing a proportion of the cobalt by nickel might present cost advantages, though only at the expense of the performance of the product.

It has now surprisingly been discovered that although a mixture of cobalt and nickel compounds of the above mentioned kind is, as already stated, inferior to pure cobalt containing compounds, compounds in which cobalt and nickel are combined in a single molecule have superior performance to those containing cobalt only.

The compounds of the present invention may be represented by the formula:

$$B(OCoA)_m(ONiA)_{3-m}$$

where the A radicals are the same or different and each in a residue of an aliphatic monocarboxylic acid of 7 to 24 carbon atoms, a resin acid, a naphthenic acid, or an aromatic carboxylic acid of 7 to 11 carbon atoms, not more than two thirds of the A radicals being a said aromatic carboxylic acid residue, and m is 0.5 to 2.5, preferably about 2.

The monocarboxylic acid used in the metal organic compounds of the present invention may be, for example, a monocarboxylic aliphatic acid, e.g. pentanoic acid, 2,2-dimethylpentanoic acid, 2-ethylpentanoic acid, 4,4-dimethylpentanoic acid, n-octanoic acid, 2,2-dimethylhexanoic acid, 2,2-ethylhexanoic acid, 4,4-dimethylhexanoic acid, 2,4,4-trimethylpentanoic acid, n-nonanoic acid, 2,2-dimethylheptanoic acid, 3,5,5-trimethylhexanoic acid, n-decanoic acid, 2,2-trimethyloctanoic acid, 7,7-dimethyloctanoic acid, n-undecanoic acid, a mixture of 2,2,2-trialkyl acetic acids known as neodecanoic or versatic acid, a resin acid such as an acid derived from wood resin, e.g. abietic acid, a naphthenic acid, or a long chain aliphatic acid such as palmitic acid, stearic acid, oleic acid, linoleic acid, linolenic acid, arachidic acid, behenic acid or tall oil fatty acid, or an aromatic acid such as for example benzoic acid or an alkyl-, alkoxy-, amino-, halogen-, thio- or hydroxy- substituted benzoic acid, e.g. salicylic acid, anthranilic acid or chlorobenzoic acid, phthalic acid, terephthalic acid, or cinnamic acid. Preferably the acid is an aliphatic acid such as neodecanoic acid or a mixture of such an acid with an aromatic acid, e.g. benzoic acid, or an acid such as octoic acid, naphthenic acid or abietic acid in a molar ratio of 2.5:0.5 to 1:2, preferably about 2:1.

The metal organic compounds of the present invention may be made by heating together a mixture in the required proportions of (1) the carboxylic acid, (2) sources of the cobalt and nickel in the required ratio such as, more especially, an oxide, hydroxide or carbonate of cobalt and nickel, (3) a borate ester of a lower alcohol, e.g. n-butanol, and (4) an acid capable of forming a volatile ester with the lower alcohol residues present in the said borate, e.g. acetic acid or propionic acid.

The volatile ester is distilled out of the reaction mixture as it is formed, preferably under reduced pressure. The acid (1) should be prereacted with the sources with cobalt and nickel (2) before the ester (3) is added.

The reaction temperature is typically in the range 50° C. to 250° C., preferably about 150° C. to 200° C. The reaction is preferably carried out under reduced pressure to facilitate removal of the volatile ester.

The metal organic compound in accordance with the present invention may be associated with a borate of an element of group IA or IIA of the periodic table, i.e. an alkali metal or alkaline earth metal. Such borates may be present at a concentration of up to 20% by weight of the metal organic compound. Suitable borates include sodium borate, potassium borate, calcium borate and magnesium borate.

The metal organic compound may also be associated with micro-crystalline wax and/or process oil to facilitate incorporation in a rubber skim stock.

The metal organic compounds of the present invention are useful in rubber skim stock as adhesion promoters. For this purpose they may be incorporated into such rubber skim stock along with conventional rubber compounding ingredients. The metal organic compound may be present in an amount between 0.2 and 2 parts by weight per 100 parts by weight of rubber and preferably the metal organic compound provides about 0.2 to 4 parts by weight of the stated combination of cobalt and nickel per 100 parts by weight of rubber.

The invention is illustrated by the following Examples, in which Examples 1, 2 and 3 are comparative and Examples 4 to 11 describes the preparation of a metal organic compound in accordance with the present invention.

EXAMPLE 1

Cobalt boro neodecanoate 283 g of cobalt hydroxide containing 62.5% by weight of cobalt was dispersed in 525 g of neodecanoic acid. Heat was evolved by the reaction and when the mixture had begun to cool down, 222 g of propionic acid was slowly added over 30 minutes and the temperature of the reaction mixture was adjusted to 95° C. After 1 hour at this temperature the mixture was heated to 190° C. and vacuum (28 mm Hg) was applied to facilitate removal of the water present in the reaction mixture. n-Butyl-o-borate (230 g) was then added slowly, following which the temperature was raised to 220° C. The n-butyl propionate formed was distilled out of the reaction mixture in vacuo. The product obtained, cobalt boro neodecanoate (786 g), contained 22.5% by weight of cobalt.

EXAMPLE 2

Nickel boro neodecanoate 561 g of nickel carbonate paste containing 31.4% of nickel was dispersed in 525 g of neodecanoic acid. The reaction mixture was heated to 60° C. and propionic acid (222 g) was then slowly added. After the propionic acid addition was complete, the mixture was heated at 95° C. for 1 hour or until carbon dioxide ceased to be evolved. The mixture was then heated to 190° C. under vacuum (28 mm Hg) until all the water formed in the reaction had been removed. n-Butyl-o-borate (230 g) was then slowly added, and the reaction mixture was heated to 220° C. in vacuo so that the n-butyl propionate formed distilled out the reaction mixture. The product obtained, nickel boro neodecanoate (880 g), contained 20% of nickel.

EXAMPLE 3

100 g of the product of Example 1 was mixed at about 50° C. with 56 g of the product of Example 2 to yield 156 g of a mixture containing 14.4% of cobalt and 7.2% of nickel.

EXAMPLE 4

196.4 g of cobalt hydroxide (60% Co) and 195.6 g of nickel carbonate paste (30% Ni) were mixed with 525 g of neodecanoic acid and the mixture was heated to 60° C. Propionic acid 222 g was then slowly added. On completion of the addition of the propionic acid the mixture was heated at 95° C. for one hour or until carbon dioxide ceased to be evolved. The mixture was then heated to 190° C. under vacuum (28 mm Hg) to remove water formed in the reaction. n-Butyl-o-borate (230 g) was then slowly added and the reaction mixture was heated to 220° C. under vacuum to remove the n-butyl propionate as it was formed. The product (841.7 g) contained 14% by weight of cobalt and 7% by weight of nickel.

EXAMPLE 5

128.7 g of technical grade nickel carbonate (45.6% Ni) was mixed with 210 g of neodecanoic acid and 259 g octoic acid and the mixture was heated to 75° C. 196 g of cobalt hydroxide (60.1% Co) was then added and once the exotherm had subsided, propionic acid 244 g was slowly added. On completion of the addition of the propionic acid the mixture was heated at 95° C. for one hour or until carbon dioxide ceased to be evolved. The mixture was then heated to 190° C. under vacuum (28 mm Hg) to remove water formed in the reaction. n-Butyl-o-borate (230 g) was then slowly added and the reaction mixture was heated to 220° C. under vacuum to remove the n-butyl propionate as it was formed. The product (752.9 g) contained 15.9% by weight of cobalt and 7.8% by weight of nickel.

EXAMPLE 6

350 g of neodecanoic acid and 350 g white sprit was heated to 75° C. 196 g of cobalt hydroxide (60.1% Co) was then added and once the exotherm had subsided, propionic acid 163 g was slowly added. On completion of the addition of the propionic acid, the mixture was allowed to cool to 30° C. 128.7 g of technical grade nickel carbonate (45.6% Ni) and 286 g naphthenic acid was added and the mixture was heated to 75° C. Propionic acid 81.4 g was then slowly added. On completion of the addition of the propionic acid the mixture was heated at 95° C. for one hour or until carbon dioxide ceased to be evolved. The mixture was then heated to 190° C. under vacuum (28 mm Hg) to remove water formed in the reaction and white spirit. n-Butyl-o-borate (230 g) was then slowly added and the reaction mixture was heated to 220° C. under vacuum to remove the n-butyl propionate as it was formed. The product (966.4 g) contained 12.5% by weight of cobalt and 6% by weight of nickel.

EXAMPLE 7

314 g of nickel propionate neodecanoate (18.7% Ni) was mixed with 175 g of neodecanoic acid, 286 g naphthenic acid and 400 g white spirit and the mixture was heated to 75° C. 196 g of cobalt hydroxide (60.1% Co) was then added and once the exotherm had subsided, propionic acid 163 g was slowly added. The mixture was then heated to 190° C. under vacuum (28 mm Hg) to remove water formed in the reaction and white spirit. n-Butyl-o-borate (230 g) was then slowly added and the reaction mixture was heated to 220° C. under vacuum to remove the n-butyl propionate as it was formed. The product (978.3 g) contained 12.7% by weight of cobalt and 6% by weight of nickel.

EXAMPLE 8

Propionic acid 160 g was slowly added to 196 g of cobalt hydroxide (60.1% Co), 350 g of neodecanoic acid and 350 g white spirit. On completion of the addition of the propionic acid, the mixture was cooled to 35° C. 122 g of benzoic acid and 128.7 g of technical grade nickel carbonate (45.6% Ni) were added and the mixture was heated to 60° C. Propionic acid 80 g was then slowly added. On completion of the addition of the propionic acid, the mixture was heated at 95° C. for one hour or until carbon dioxide ceased to be evolved. The mixture was then heated to 190° C. under vacuum (28 mm Hg) to remove water formed in the reaction and white spirit. n-Butyl-o-borate (230 g) was then slowly added and the reaction mixture was heated to 220° C. under vacuum to remove the n-butyl propionate as it was formed. The product (736 g) contained 15.6% by weight of cobalt and 8% by weight of nickel.

EXAMPLE 9

175 g of neodecanoic acid, 122 g benzoic acid and 350 g white spirit were heated to 50° C. 196 g of cobalt hydroxide (60.1% Co) was then added and once the exotherm had subsided, 164 g of propionic acid was added quickly. On completion of the addition of the propionic acid the mixture was heated to 150° C. 314 g of nickel propionate neodecanoate (18.7% Ni) was then added. The mixture was then heated to 190° C. under vacuum (28 mm Hg) to remove water formed in the reaction and white spirit. n-Butyl-o-borate (230 g) was then slowly added and the reaction mixture was heated to 220° C. under vacuum to remove the n-butyl propionate as it was formed. The product (760 g) contained 15.8% by weight of cobalt and 7.9% by weight of nickel.

EXAMPLE 10

Propionic acid 164 g was slowly added to 196 g of cobalt hydroxide (60.1% Co), 350 g of neodecanoic acid and 350 g white spirit. On completion of the addition of the propionic acid, the mixture was heated at 100° C. for 30 minutes. The mixture was then cooled to 70° C. and 302 g of abietic acid and 128.7 g of technical grade nickel carbonate (45.6% Ni) were added. Propionic acid 80 g was then slowly added. On completion of the addition of the propionic acid the mixture was heated at 95° C. for one hour or until carbon dioxide ceased to be evolved. The mixture was then heated to 190° C. under vacuum (28 mm Hg) to remove water formed in the reaction and white spirit. n-Butyl-o-borate (230 g) was then slowly added and the reaction mixture was heated to 220° C. under vacuum to remove the n-butyl propionate as it was formed. The product (946 g) contained 12.5% by weight of cobalt and 6.6% by weight of nickel.

EXAMPLE 11

175 g of neodecanoic acid, 302 g abietic acid and 350 g white spirit were heated to 70° C. 196 g of cobalt hydroxide (60.1% Co) was then added and once the exotherm had subsided 164 g of propionic acid was slowly added. On completion of the addition of the propionic acid the mixture was heated to 150° C. 314 g of nickel propionate neodecanoate (18.7% Ni) was then added. The mixture was then heated to 190° C. under vacuum (28 mm Hg) to remove water formed in the reaction and white spirit. n-Butyl-o-borate (230 g) was then slowly added and the reaction mixture was heated to 220° C. under vacuum to remove the n-butyl propionate as it was formed. The product (943 g) contained 12.8% by weight of cobalt and 6.4% by weight of nickel.

The products of Examples 1 to 11 were tested as rubber adhesion promoters as follows.

A rubber skim stock was prepared having the following composition:

|  | Part by Weight |
|---|---|
| Natural Rubber SMR 10 | 100.00 |
| Peptiser (P.C.T.P.)[a] | 0.12 |
| HAF Carbon Black N-326 | 55.00 |
| Zinc oxide | 8.00 |
| Stearic acid | 0.5 |
| Highly Aromatic Process Oil | 3.00 |
| Antidegradant (6 pPD)[b] | 2.00 |
| Accelerator (DCBS)[c] | 0.7 |
| Insoluble Sulphur | 4 |

[a] Zinc salt of pentachlorothiophenol
[b] N-(1,3-dimethylbutyl)-N'phenyl-p-phenylene diamine
[c] N,N-Dicyclohexyl-2-benzthiazyl sulphenamide.

Vulcanisable compositions were prepared using the above rubber skim stock and the adhesion promoters described in Examples 1 to 11 above. Each promoter was added in a proportion to provide 0.15 parts by-weight of metal or mixture of metals per 100 parts by weight of rubber. The adhesion promoters were added to the skim stock during mixing in a 1.5 l laboratory internal mixer and sheeted off on to a 2-roll laboratory mill. All the compositions were vulcanised to $T_{90}$+six minutes at 153° C.

Adhesion tests were carried out using a modified static block pull test based upon ASTM D2229 using an embedment length of 10 mm. Typical brass coated steel tyre cord of the construction 2+2×0.25 from Bekaert was used, each cord having a coating of brass with an average copper content of 63.5%. Adhesion values are quoted as a percentage of the value obtained with the product of Example 1. The results are given in Table 1.

| PROMOTER PRODUCT OF EXAMPLE | UNAGED | HEAT AGED |
|---|---|---|
| 1 (comparative) | 100 | 100 |
| 2 (comparative) | 88.3 | 86.6 |
| 3 (comparative) | 92.5 | 97.5 |
| 4 | 105 | 125 |
| 5 | 115 | 118 |
| 6 | 113 | 121 |
| 7 | 105 | 122 |
| 8 | 98.6 | 122 |
| 9 | 107 | 118 |
| 10 | 107 | 125 |
| 11 | 104 | 130 |

These results show that, whereas the mixture of cobalt and nickel compound is less effective as an adhesion promoter both unaged and after heat aging, than a compound based on cobalt only, the metal organic compound of the invention containing both cobalt and nickel in the same molecule is surprisingly more effective as an adhesion promoter than the compound containing only cobalt both unaged and after heat aging.

We claim:

1. A metal organic compound of average formula:

$$B(OCoA)_m(ONiA)_{3-m}$$

where the A radicals are the same or different and each is a residue of an aliphatic monocarboxylic acid of 7 to 24 carbon atoms, a resin acid, a naphthenic acid, or an aromatic carboxylic acid of 7 to 11 carbon atoms, not more than two thirds of the A radicals being a said aromatic carboxylic acid residue, and m is 0.5 to 2.5.

2. A metal organic compound according to claim 1 wherein m is about 2.

3. A metal organic compound according to claim 1 wherein A is a residue of neodecanoic acid, alone or in admixture with one or more of octoic acid, naphthenic acid, benzoic acid, and abietic acid.

4. A metal organic compound according to claim 1, associated with up to 20% by weight of a borate of a metal of group IA or IIA of the periodic table.

5. A metal organic compound according to claim 1, associated with microcrystalline wax and/or process oil.

* * * * *